(12) United States Patent  
Theilacker et al.

(10) Patent No.: US 8,500,691 B2  
(45) Date of Patent: Aug. 6, 2013

(54) METHOD FOR PRODUCING A HEATING DEVICE HAVING A HEATING PROFILE FOR MEDICAL INSTRUMENTS AND A HEATING DEVICE PRODUCED BY THAT METHOD

(75) Inventors: Matthias Theilacker, Stuttgart (DE); Wolfgang Theilacker-Beck, Stuttgart (DE)

(73) Assignee: WWT Technischer Geraetebau GmbH, Stuttgart (DE)

( * ) Notice: Subject to any disclaimer, the term of this patent is extended or adjusted under 35 U.S.C. 154(b) by 317 days.

(21) Appl. No.: 12/656,660

(22) Filed: Feb. 12, 2010

(65) Prior Publication Data  
US 2010/0145273 A1   Jun. 10, 2010

Related U.S. Application Data

(63) Continuation of application No. 11/822,891, filed on Jul. 11, 2007, now abandoned.

(30) Foreign Application Priority Data

Jul. 14, 2006   (DE) .......................... 10 2006 032 775

(51) Int. Cl.  
*A61F 7/12*   (2006.01)

(52) U.S. Cl.  
USPC .......................................................... 604/113

(58) Field of Classification Search  
USPC .................. 604/113, 114; 264/514, 539, 540, 264/142, 171.11, 171.21, 173.12, 173.16, 264/176.1, 209.6, 209.7, 3.3, 13, 452, 464  
See application file for complete search history.

(56) References Cited

FOREIGN PATENT DOCUMENTS

| DE | 4241830 A1 | * | 6/1994 |
| DE | 102005036369 A1 | * | 2/2007 |

* cited by examiner

*Primary Examiner* — Nicholas Lucchesi  
*Assistant Examiner* — Pritesh Patel  
(74) *Attorney, Agent, or Firm* — Paul Vincent

(57) ABSTRACT

A method for producing a temperature control means (5c, 5c) of an elastic heating profile (1), which heat and/or cool a medical instrument inserted into a cavity (3) of the heating profile (1), are provided in bores (4a, 4b, 4c, ...) having a bore diameter (110, 110') which is smaller than the outer diameter (120, 120') of the temperature control means (5c, 5e) to be inserted into the bores (4a, 4b, 4c, ...). A positive and/or non-positive connection between the heating profile (1) and the received temperature control means ensures good thermal contact. The production costs for an operable heating profile or temperature control means are also reduced.

11 Claims, 2 Drawing Sheets ated by reference.
METHOD FOR PRODUCING A HEATING DEVICE HAVING A HEATING PROFILE FOR MEDICAL INSTRUMENTS AND A HEATING DEVICE PRODUCED BY THAT METHOD This application is a continuation of Ser. No. 11/822,891 filed Jul. 11, 2007 now abandoned and also claims Paris Convention priority of DE 10 2006 032 775.6 filed Jul. 14, 2006 the complete disclosures of which are hereby incorporated by reference.

BACKGROUND OF THE INVENTION

The invention relates to a method for producing an elastic heating device having a heating profile designed to enclose and control the temperature of medical instruments, comprising at least one cavity that extends axially along the heating profile and can be accessed from the outside, for inserting a medical instrument, and at least one axial bore that extends along the entire length of the heating profile, for receiving a temperature control means.

Heating devices of this type are used to cool, heat and/or maintain a defined temperature of medical instruments, e.g. infusion tubes, and liquids or gases that flow through them.

A heating device of this type is disclosed e.g. in DE 827 702. A tube used for injecting medical solutions is surrounded along its entire length by channels in which a heating agent is circulated, wherein the heating agent channels are formed by one or more tubes. In order to enclose almost the entire periphery of the injection tube, several tubes are connected to each other through vulcanization, which can impair the heat transfer from the heating profile to the tube.

A further heating device, which is shown and described in DE 4 241 830 A1, has a heating profile designed as a one-piece jacket which comprises a continuous channel for receiving an infusion tube. The received infusion tube is surrounded inside the channel by an electrically heatable heat transfer body of metal. This can reduce the flexibility of the heating profile and its adjustability to the conditions at the location of use.

DE 4 444 180 C2 discloses a heating device using a heating profile having the shape of a slotted tube in which heating wires or heating fluid channels are embedded. The heating profile is produced as a section of an endless profile into which the temperature control means are inserted, embedded or vulcanized. Later introduction of the temperature control means into a section of the endless profile requires additional production steps, such as insertion of heating wires. Good thermal transfer from the temperature control means to the heating profile can thereby not be ensured. Direct insertion of the heating wires, e.g. through vulcanization, increases the overall production expense, since e.g. the follow-up work for exposing the electrical temperature control means requires significant time and work.

A further development of this heating profile which is disclosed in DE 299 17 247 U1 has grooves for inserting and holding the infusion tube. This ensures good thermal transfer from the heating profile to an inserted infusion tube. Insertion of heating elements into bores of the groove flanks, as disclosed in DE 4 444 180 C2, reduces the efficiency of thermal transfer from the heating elements to the heating profile.

It is the underlying purpose of the invention to introduce a method for the production of a heating device having a heating profile which ensures good thermal contact between the temperature control means and the flexible heating profile, and which also permits provision of the temperature control means independently of the heating profile being produced.

SUMMARY OF THE INVENTION

This object is achieved with a method for producing a heating device which covers and controls a temperature of a medical instrument, the method comprising the steps of:
a) preparing a heating profile from an elastic material, the heating profile having at least one cavity which extends along an axial extension thereof and which can be accessed from an outside for insertion of the medical instrument, and with at least one axial bore which extends along an entire length of the heating profile, the at least one axial bore having an axial bore diameter;
b) selecting a temperature control element, the temperature control element having an outer surface with an outer surface diameter that is larger than the axial bore diameter; and
c) pressing, following steps a) and b), the temperature control element into the axial bore of the heating profile, thereby widening the axial bore, wherein the widened axial bore presses inwardly in a substantially radial direction against the outer surface of the temperature control element, thereby establishing good thermal contact between the temperature control element and the heating profile.

The bore diameter in accordance with the invention is the inner diameter of the bore in the relaxed state, i.e. without inserted temperature control means. Due to the undersize of the bore compared to the maximum outer diameter of the temperature control means to be inserted into the bore, the bore must be widened or extended for inserting the temperature control means. After insertion of the temperature control means, the elastic material of the heating profile preferably surrounds the overall peripheral surface of the temperature control means. The natural compression of the widened bore produces a radial force that acts on the overall periphery of the inserted temperature control means. The temperature control means is pressed into the flexible heating profile in a positive and/or non-positive fashion. This ensures good thermal contact between the temperature control means and the heating profile. Another advantage results from the fact that the temperature control means is securely held in the heating profile and cannot slip or fall out. The inventive heating profile is produced without temperature control means, typically as an extruded profile, into which the temperature control means are subsequently pressed. With this production method, the temperature control means can be machined independently of the heating profile and no time-consuming manual work or additional work steps are required in order to provide an operational heating profile. The flexible heating profile is produced from plastic material or rubber, preferably silicon. The length of the heating profile is typically 100 to 200 cm, the diameter of the single-layered profile is approximately 15 mm. A temperature control device or temperature control system in accordance with the invention comprises the elastic heating profile and at least one temperature control means to be inserted into the heating profile.

In a preferred embodiment of the inventive method, the heating profile has several bores, in particular, of different bore diameters. The bores generally have a round cross-section but may also be elliptical or have an angular cross-section. The bores are preferably uniformly distributed around the cavity enclosed by the heating profile. Different temperature control means, such as heating conductors and temperature sensors, may be inserted into the bores. The inventive heating profile of this embodiment may be divided into zones of different heating power.

In a further preferred embodiment of the invention, at least one, and preferably two bores are provided in the heating profile, which extend along or nearly along a neutral bending line (neutral fiber) of the heating profile when the heating profile is bent. The bore is suitably provided in the neutral fiber in order to avoid contraction or extension in the longitudinal direction of a temperature control means introduced into the bore when the heating profile is bent. It is almost impossible to prevent bending of the heating profile during the intended use, e.g. guiding an infusion tube from a container containing the infusion to a patient. Introduction of sensitive temperature control means into a bore whose length does not vary when the heating profile is bent, prevents great strain and, in particular, damage due to excessive strain on the sensitive temperature control means.

The inventive heating profile is advantageously produced from a heat conducting material. The heating profile acts as a heat conductor between the temperature control means inserted into the bores and the medical instrument received in the cavity. The medical instrument, e.g. an infusion tube is heated and/or cooled by the temperature control means. The temperature in or on the infusion tube can be determined by temperature probes. The heating conductors and temperature sensors are advantageously connected to a control and regulation unit.

In a preferred embodiment, the heating profile has a coating of a heat-insulating material on its outer surface, which is preferably connected to the material of the heating profile with material fit. The coating, which serves as an insulation layer, prevents thermal loss to the outside or uncontrolled thermal influence from the outside to the inside to the medium to be heated in the medical instrument. In order to optimize the insulation effect of the outer layer, the outer layer is undetachably connected to the heat-conducting and/or heat-storing inner region of the heating profile. The two layers are directly connected with material fit to minimize formation of folds due to bending of the heating profile, which could impair the insulation effect of the outer layer. The coating can be applied later e.g. by foaming. The heating profile is, however, advantageously produced from two layers of two different materials in one work step by extruding the two layers together. This co-extrusion produces a direct, undetachable connection between the insulating outer layer and the thermally conducting inner layer of the heating profile, such that the insulation layer is almost undetachably connected to the heating profile and need not be fixed thereto later at great expense. Heating profiles of the most different types can be coated with a heat-insulating material to constitute an individual inventive concept independent of the inventive features of the independent claim. Elastic heating profiles which are foamed and/or coated with material fit have the advantages of this embodiment even when they do not have a bore.

An advantageous embodiment of the inventive method is characterized in that the cavity is formed as a groove for receiving an infusion tube or a trocar. The infusion tube or the trocar can be inserted into the cavity via a slot or opening that extends along the axial direction of the heating profile. The cavity may, however, also be accessed via a slot which is cut for inserting or introducing the infusion tube or trocar. The groove is designed like a counter-piece, i.e. its shape is adjusted to the medical instrument to be inserted, and advantageously undersized compared to the dimensions of the instrument. This generates stress in the heating profile when the infusion tube is inserted, resulting in a force that acts radially on the infusion tube. The infusion tube is held in the heating profile in a positive and/or non-positive fashion, thereby ensuring both good thermal contact between the heating profile and the infusion tube and stationary mounting of the heating profile to the infusion tube. The groove is designed such that the heating profile surrounds or covers the received infusion tube on almost its entire outer peripheral surface, and the insertion opening is largely closed again. The opening gap has a minimum size in order to largely prevent heat from escaping through the gap during operation of a heating means with the inventive heating profile as well as uncontrolled heat input from the outside through this gap. An insulation layer is advantageously provided on the outer surface right up to the boundary of insertion opening or insertion gap.

In addition, a temperature control means is provided in at least one bore. The temperature control means is/are advantageously designed as an electric heating means, such as heating conductors or heating wires and/or sensors, e.g. temperature probes. The heating wires are typically designed as helices, and when they are introduced into and returned from a bore, as double helices. The temperature sensors or temperature probes are generally designed as NTC resistances. The inventive heating profile can be finished and provided ready for use in dependence on the application by selecting corresponding heating or cooling means and corresponding measuring means, e.g. for heating, cooling or insulation. The bores may also serve as fluid channels for heating or cooling agents. The heating means are thereby advantageously provided in bores along the neutral bending lines. When a heating conductor is inserted into a bore which is length-invariant during bending of the heating profile, i.e. along the neutral fiber, it is largely free from bending loads, such as extension and compression.

Further advantages of the invention can be extracted from the figures and the description of the drawing. The drawing shows embodiments of the inventive heating profile. The features shown in the figures are only schematic and are not to be taken to scale

DESCRIPTION OF THE PREFERRED EMBODIMENT

Figure 1:
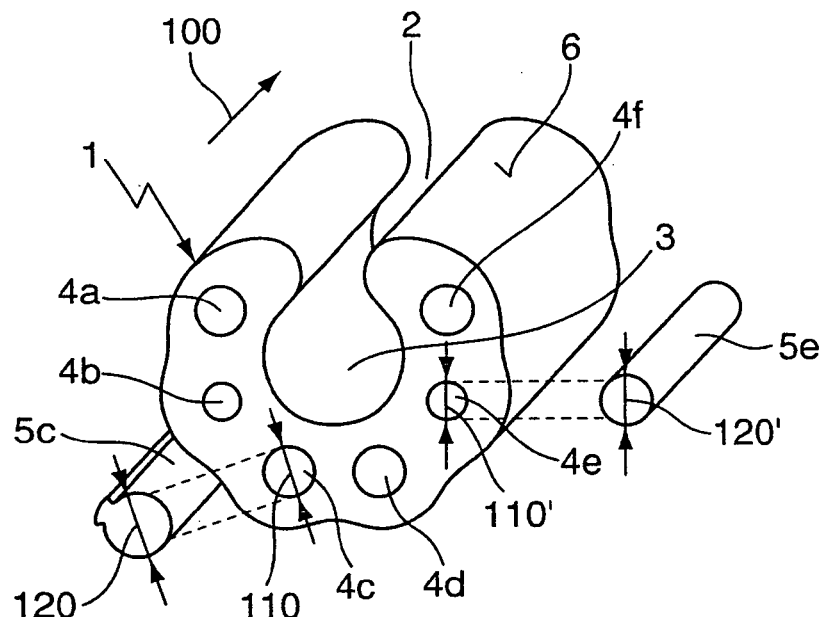
FIG. 1 shows an embodiment of the inventive heating profile.

FIG. 1 shows a perspective view of a section of a substantially cylindrical heating profile 1. The heating profile 1 has an opening 2, a cavity 3, and axial bores 4a, 4b, 4c, 4d, 4e and 4f along its entire length. The cavity 3 is circularly surrounded by the heating profile 1 except for an interruption at the opening 2. The bores 4a, 4b, . . . are embedded in the profile wall, and are oriented in the axial direction 100 along the longitudinal extension of the heating profile 1, like the opening 2 and the cavity 3. The bores 4a, 4b, . . . are disposed at almost regular intervals around the cavity 3, wherein the bores 4a, 4c, 4d and 4f have a bore diameter which corresponds to a bore diameter 110 of the bore 4c, is larger than the bore diameter of the bores 4b and 4e, and corresponds to a further bore diameter 120' of the bore 4e. A first temperature control means 5c and a second temperature control means 5e are shown on each side of the heating profile 1. The outer surface 6 of the heating profile 1 has a wavy contour.

The first temperature control means 5c is designed as a temperature sensor having a first outer diameter 120. The second temperature control means 5e is a heating conductor with a second outer diameter 120'. The heating profile 1 is shown as a blank, i.e. without inserted temperature control means 5c and 5e, and the bore diameters 110 and 110' are shown in the relaxed state without compression. The bore diameter 110 of the bore 4c is smaller than the first outer diameter 120 of the first temperature control means 5c, such that the bore 4c must be widened or extended for inserting the first temperature control means 5c. The further bore diameter 110' of the bore 4e and the second outer diameter 120' of the second temperature control means 5e have a corresponding ratio of dimensions.

Figure 2:
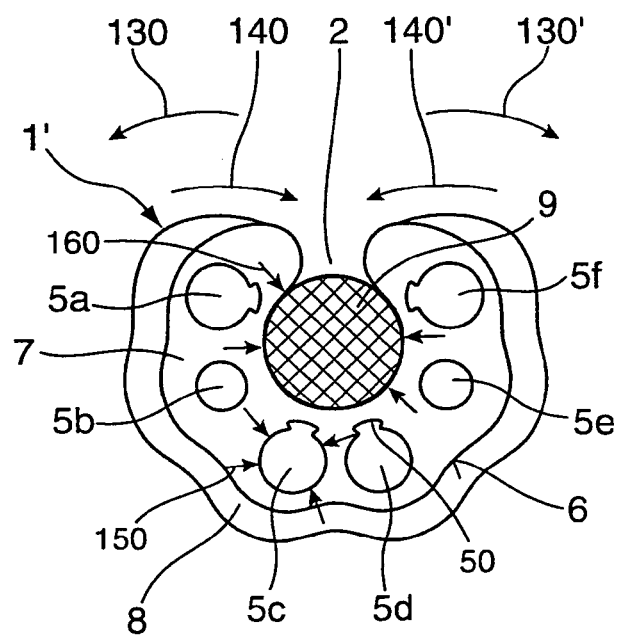
FIG. 2 shows a cross-section through a further embodiment of the inventive heating profile.

The heating profile 1' shown in cross-section in FIG. 2 differs from that of FIG. 1 in that a coating 8 is provided on the outer surface 6 which defines an inner region 7 of the heating profile 1'. The coating 8 which is disposed by foaming around the inner area 7 consists of a heat-insulating material. A medical instrument 9, in the present case an infusion tube having a circular cross-section, is inserted into the heating profile 1'. The opening 2 is widened by an opening force in the opening direction 130 and 130' in order to insert or press-in the medical instrument 9. The material stress in the heating profile 1' produces a restoring force in the closing direction 140 and 140', which largely closes the opening 2 again after the insertion process. The material and the shape of the heating profile 1' are selected such that the medical instrument 9 is jacketed in a positive engagement fashion by the inner area 7, and a radial force (e.g. indicated by arrow 160) acts on the medical instrument 9. Due to this frictional connection, the medical instrument 9, the infusion tube, is safely held in the heating profile 1', such that it cannot slip out of it.

Temperature control means 5a, 5c, 5d, and 5f designed as temperature sensors and temperature control means 5b and 5e designed as heating conductors are inserted into the heating profile 1'. The temperature control means 5a, 5c, 5d and 5f designed as temperature sensors each have a sensor head 50 indicated e.g. on the temperature control means 5d, which is directed towards the center of the heating profile 1' and the medical instrument 9 inserted at that location. The elastic, extendable heating profile 1' abuts the temperature control means 5a, 5b, . . . in a positive fashion and with compression force fit, thereby fixing them in the heating conductor 1'. The radial compression force is indicated on the first temperature control means 5c e.g. by arrow 150.

Figure 3:
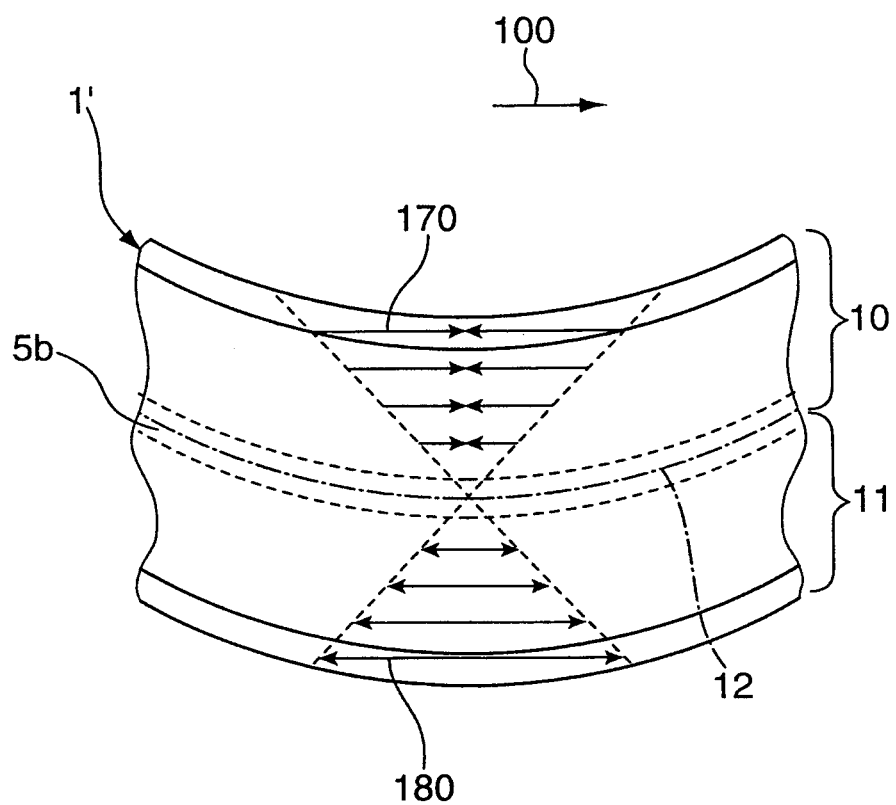
FIG. 3 shows a longitudinal section through a short section of the inventive heating profile of FIG. 2.

FIG. 3 shows a longitudinal section through the heating profile 1'. The heating profile 1', which extends in the axial direction 100, is bent, thereby defining a compression area 10 and an extension area 11 in the heating profile 1'. The heating profile 1' is compressed in the compression area 10 due to pressure load (as indicated by arrow pair 170). The heating profile 1' is extended in the extension area due to tensile load (as indicated by arrow pair 180). The length of a neutral bending line 12 that extends on the boundary line between the compression area 10 and the extension area 11 does not change when the heating profile 1' is bent. For this reason, the temperature control means 5b, which is disposed along the neutral bending line 12, is hardly compressed or stretched and thereby remains nearly free from bending loads.

The neutral fiber (neutral bending line 12), whose length does not vary when the heating profile is bent, (neutral bending line 12) can be fixed by inserting a temperature control means (e.g. temperature control means 5b in FIG. 3) of a material which is considerably less elastic than the material of the heating profile. The solidity and flexibility of the temperature control means is thereby selected such that, when the heating profile is bent or curved in dependence on the application, the temperature control means follows the bending shape largely unchanged, while the surrounding material of the heating profile is extended or compressed (compression area 10 and extension area 11). The heating profile is moreover not extended or compressed in an axial direction. In other words, its length does not vary. All other bores, i.e. those outside of the neutral fiber, have flexible feed lines. Fixing of a neutral fiber via a temperature control means, which is rigid compared to the heating profile, can be realized with heating profiles of the most different types independently of a heating profile comprising the features of claim 1, and represents a separate inventive concept. The heating profile with defined bending behavior in accordance with the invention has at least one bore for receiving a temperature control means. It is also feasible to define several, preferably two neutral bending lines on the heating profile via corresponding temperature control means in the heating profile.

The temperature control means 5c, 5c of an elastic heating profile 1 are provided in bores 4a, 4b, 4c, . . . for heating and/or cooling a medical instrument which is inserted into a cavity 3 of the heating profile 1, the bores having a diameter 110, 110' which is smaller than the outer diameter 120, 120' of the temperature control means 5c, 5e to be introduced into the bores 4a, 4b, 4c, . . . . A positive and/or non-positive connection between the heating profile 1 and the received temperature control means ensures good thermal contact. The production costs for an operable heating profile or temperature control means are moreover reduced.

We claim:

1. A method for producing a heating device which covers and controls a temperature of a medical instrument, the method comprising the steps of:
    a) co-extruding, in a single extrusion process, an inner heating profile, made from a heat-conducting elastic material, and an outer coating, made from a heat-insulating material, an inner surface of the outer coating thereby being connected to an outer surface of the heating profile with material fit, wherein the heating profile and the outer coating define at least one cavity which extends along an entire axial extension thereof and which can be accessed from an outside for insertion of the medical instrument and the heating profile defining at least one axial bore which extends along an entire length thereof, the at least one axial bore having an axial bore diameter, wherein the cavity and the axial bore are separated from each other, along an entire axial length of the heating profile, by a thickness of the elastic material from which the heating profile is made;
    b) selecting a temperature control element, the temperature control element having an outer surface with an outer surface diameter that is larger than the axial bore diameter; and
    c) inserting, following steps a) and b), the temperature control element into the axial bore of the heating profile, thereby widening the axial bore, wherein the widened axial bore presses inwardly in a substantially radial direction against the outer surface of the temperature control element thereby establishing good thermal contact between the temperature control element and the heating profile.

2. The method of claim 1, wherein several bores are provided in the heating profile.

3. The method of claim 2, wherein the bores have different bore diameters.

4. The method of claim 1, wherein at least one bore is provided in the heating profile which extends along or substantially along a neutral bending line of the heating profile when the heating profile is bent.

5. The method of claim 4, wherein there are two bores.

6. The method of claim 1, wherein the cavity is designed as a groove for receiving an infusion tube or a trocar.

7. The method of claim 1, wherein the temperature control means is disposed in at least one bore.

8. The method of claim 7, wherein the temperature control means is designed as an electric heating means, a heating conductor, a heating wire, a sensor, or a temperature probe.

9. The method claim 8, wherein the temperature control means is disposed along a neutral bending line.

10. The heating device produced by the method of claim 1.

11. The heating profile produced by the method of claim 1.

* * * * *